(12) United States Patent
Cho et al.

(10) Patent No.: US 8,428,673 B2
(45) Date of Patent: Apr. 23, 2013

(54) MEDICAL MEASURING DEVICE

(75) Inventors: Ok Kyung Cho, Schwerte (DE); Yoon Ok Kim, Schwerte (DE)

(73) Assignee: Ingo Flore, Dortmund (DE)

( * ) Notice: Subject to any disclaimer, the term of this patent is extended or adjusted under 35 U.S.C. 154(b) by 1351 days.

(21) Appl. No.: 11/990,317

(22) PCT Filed: Aug. 9, 2006

(86) PCT No.: PCT/EP2006/007874
§ 371 (c)(1),
(2), (4) Date: Mar. 10, 2008

(87) PCT Pub. No.: WO2007/017263
PCT Pub. Date: Feb. 15, 2007

(65) Prior Publication Data
US 2009/0253968 A1    Oct. 8, 2009

(30) Foreign Application Priority Data

Aug. 9, 2005 (DE) .......................... 10 2005 038 035
Oct. 25, 2005 (DE) .......................... 10 2005 051 030

(51) Int. Cl.
*A61B 5/1455* (2006.01)
(52) U.S. Cl.
USPC ........................................................ 600/323
(58) Field of Classification Search .................. 600/309, 600/310, 322–324, 500, 509, 547, 549
See application file for complete search history.

(56) References Cited

U.S. PATENT DOCUMENTS

| | | | |
|---|---|---|---|
| 4,928,014 A | 5/1990 | Rosenthal | |
| 4,960,126 A | 10/1990 | Conion et al. | |
| 5,237,178 A | 8/1993 | Rosenthal et al. | |
| 6,331,162 B1 | 12/2001 | Mitchell | |
| 6,595,918 B2 * | 7/2003 | Gopinathan et al. | 600/300 |
| 6,714,814 B2 | 3/2004 | Yamada et al. | |
| 6,790,178 B1 | 9/2004 | Mault et al. | |
| 2004/0034293 A1 * | 2/2004 | Kimball | 600/323 |

(Continued)

FOREIGN PATENT DOCUMENTS

| | | |
|---|---|---|
| EP | 1 491 134 | 12/2004 |
| WO | WO 99/62399 | 12/1999 |
| WO | WO 00/69328 | 11/2000 |

OTHER PUBLICATIONS

International Search Report.

(Continued)

*Primary Examiner* — Max Hindenburg
(74) *Attorney, Agent, or Firm* — Collard & Roe, P.C.

(57) ABSTRACT

The invention relates to a measuring device (1) for the non-invasive measurement of physiological parameters. The measuring device (1) is suited to detect and localize by way of self diagnosis diseases such as, for example, inflammations, tumors or arteriosclerosis. The invention proposes a measuring device (1) with at least one optical measuring unit (100) for the generation of oximetric and/or plethysmographic measuring signals, an evaluation unit (140) processing the measuring signals, and a unit (120, 130) for the acquisition of local tissue parameters such as fat content, water content and/or blood perfusion, with the evaluation unit (140) being designed such that at least one local metabolic parameter is determined, in particular the local oxygen consumption, from the signals furnished by the optical measuring unit and obtained from tissue parameters. Moreover, the measuring device (1) enables the non-invasive determination of the blood glucose level.

39 Claims, 5 Drawing Sheets

U.S. PATENT DOCUMENTS

2004/0225209 A1* 11/2004 Cho et al. .................... 600/365
2005/0177062 A1* 8/2005 Skrabal et al. ............... 600/547
2006/0155193 A1* 7/2006 Leonardi et al. ............. 600/473

OTHER PUBLICATIONS

Nitzan et al., "Infrared radiometry of thermally insulated skin for the assessment of skin blood flow," Optical Engineering, Sep. 1994, vol. 33, No. 9, pp. 2953-2956. (Spec, p. 5).

Cho et al., "Noninvasive Measurement of Glucose by Metabolic Heat Conformation Method," Clinical Chemistry, International Journal of Laboratory Medicine and Molecular Dianostics, 2004, vol. 50, No. 10, pp. 1894-1898. (Spec, p. 19).

Lepretre et al., "Effect of Exercise Intensity on Relationship between $VO_{2max}$ and Cardiac Output," Official Journal of the American College of Sports Medicine, 2004, pp. 1357-1363. XP-002428499. (ISR).

* cited by examiner

MEDICAL MEASURING DEVICE

CROSS REFERENCE TO RELATED APPLICATIONS

Applicants claim priority under 35 U.S.C. §119 of German Application No. 10 2005 038 035.2 filed Aug. 9, 2005 and German Application No. 10 2005 051 030.2 filed Oct. 25, 2005. Applicants also claim priority under 35 U.S.C. §365 of PCT/EP2006/007874 filed Aug. 9, 2006. The international application under PCT article 21(2) was not published in English.

The invention relates to a measuring device for the non-invasive determination of physiological parameters, with said device being provided with at least one optical measuring unit generating oximetric and/or plethysmographic measuring signals, and with an evaluation unit for processing the measuring signals.

As is a known fact, supplying the body tissue with oxygen counts among the most important vital functions of human beings. Therefore, oximetric diagnosis modalities have been of great significance in the medical field in these days. Routinely, so-called pulse oximeters employed for this purpose. Such pulse oximeters typically comprise two light-emitting sources radiating red and infrared light of different wavelength into the body tissue. The light is scattered in the body tissue and partly absorbed. The scattered light is finally detected by means of a light sensor in the form of a suitable photocell. On the one hand, commercially available pulse oximeters typically use light within a wavelength range of 660 nm. In this range the light absorption of oxihemoglobin and deoxihemoglobin varies greatly. Accordingly, the intensity of the scattered light detected by means of a photo sensor differs based on how thoroughly the examined body tissue is supplied with oxygen-rich or oxygen-deficient blood. On the other hand, light in the wavelength range of 810 nm is usually employed. This light wavelength is in the so-called near-infrared spectral range. The light absorption of oxihemoglobin and deoxihemoglobin in this spectral range is essentially identical. Moreover, the known pulse oximeters are capable of generating a plethysmographic signal, i.e. a volume pulse signal, that is indicative of the blood volume that varies with a heartbeat in the microvessel system examined by means of the pulse oximeter (so-called photoplethysmography). Using different light wavelengths in the above mentioned spectral ranges enables the oxygen content of the blood (oxygen saturation) to be to concluded based on the different light absorption characteristics. Customary pulse oximeters are either clipped onto the finger tip or earlobe of a patient. Based on the blood perfusion of the microvessel system in these areas of body tissue the volume pulse signal is generated.

An oximetric diagnosis device that has highly flexible usage qualities is known from WO 00/69328 A1. This prior-art device is designed for hand-guidance so that it can be used on optional measuring sites on the human body. This prior-art device thus permits the body of a patient to be systematically scanned so to speak. Fixing or securing the diagnosis device as is usually done with customary pulse oximeters can be omitted with the device disclosed by the above cited publication.

Furthermore, the above stated WO 00/69328 A1 elucidates the usefulness of the oximetric diagnosis device for the spatially resolved diagnosis of inflammations, tumors and arteriosclerosis diseases in the skin-near body tissue of a patient. Diseases of this nature cause a variation of the flow of blood through body tissue. By performing a spatially resolved oximetric scanning of the body with said prior-art device such blood flow variations which are indicative of a disease of the nature mentioned above can thus be diagnosed and localized.

The ECG (electrocardiogram) is presumably the most frequently applied examination modality for the diagnosis of cardiovascular diseases. By means of an ECG unit electrical signals are transmitted from the body of the patient to be examined via two or more ECG electrodes. The ECG thus obtained reflects the bioelectric voltage situation prevailing during the spread of stimulus and repolarization at the heart. The ECG includes a variety of parameters that can be evaluated for diagnostic purposes. At the time the heart muscle contracts during a heartbeat the ECG shows a distinctive peak which is also termed R-peak. Moreover, the ECG also shows the so-called P wave which precedes the R peak. The R peak in turn is followed by the so-called T wave. The minima shown in the ECG arising immediately before and after the R peak are termed Q and S. Parameters of interest for cardiovascular diagnostics are the duration of the P wave as well as the amplitude of the P wave, the duration of the PQ interval, the duration of the QRS complex, the duration of the QT interval as well as the amplitude of the T wave. Both the absolute values of the parameters mentioned and the relationship between these parameters provide information based on which the health state of the cardiovascular system can be determined. Devices and methods for ECG recordings are known, for example, from publications U.S. Pat. No. 6,331,162 or U.S. Pat. No. 4,960,126 describing prior art.

Other physiological parameters, such as the body fat content for example, may be determined by bioelectric impedance measurement, as is for example known from U.S. Pat. No. 6,714,814. However, the composition of the body tissue may also be determined by optical methods. The principle of determining the body fat content optically by means of infrared light has been described in U.S. Pat. No. 4,928,014 for example.

It is thus the objective of the present invention to provide a device for the non-invasive determination of physiological parameters that constitute an improvement over prior-art technology and has been enhanced with respect to its functionality. In particular, a device is proposed that enables a reliable as possible diagnosis and localization of diseases such as inflammations, tumors or cancer diseases (skin cancer, melanoma) as well as angiopathy. Optionally, the device shall also enable the (cardiovascular) fitness of a user to be assessed. For this purpose, the device shall also be suited for self-diagnostic purposes.

Proceeding from a measuring device of the kind first mentioned above the invention meets this objective by providing for the evaluation unit to be designed such that at least one local metabolism parameter is determined, especially the local oxygen consumption, from the signals furnished by the local measuring unit.

Central idea of the invention is to use the oximetric and/or plethysmographic measuring signals obtained by means of the optical measuring unit in order to determine not only the local oxygen concentration at the relevant measuring site—as is done with customary oximetric diagnostic equipment—but, in particular, also the local oxygen consumption which is an important indicator of the local metabolic activity. From pathological changes in the metabolism diseases can be detected and localized by means of the measuring device according to the invention.

According to a preferred configuration the inventive measuring device is additionally provided with a unit for recording local tissue parameters such as fat content, water content and/or blood perfusion, with the evaluation unit in this case being designed such that at least one local metabolic parameter is determined from the signals furnished by the optical measuring unit and obtained from tissue parameters.

Within the scope of the invention blood perfusion, for example, is an important local tissue parameter or, to be more precise, the perfusion-related volume variations of the body tissue examined. For the purpose of determining perfusion the inventive measuring device may thus be provided with a plethysmographic unit of customary design (e.g. a photoplethysmograph). In this manner the optical measuring unit of the inventive measuring device may be utilized to simultaneously determine local tissue parameters.

The invention is based, inter alia, on findings according to which it is possible by combining the detection of oximetric and plethysmographic signals to determine local metabolic parameters.

For the purpose of determining the local oxygen consumption by means of the inventive measuring device it should also be possible to ascertain the capillary oxygen concentration in the tissue in addition to the oximetrically determined arterial oxygen concentration. However, in this context the composition of the body tissue examined must be known. Decisive parameters are the local fat content and/or water content of the body tissue. These parameters can be detected by a bioelectric impedance measurement, for example. As per an expedient configuration of the invention a customary (optical) oximetry unit is combined with a bioelectric impedance measuring unit to form a single device. Based on the measuring signals received from the bioelectric impedance measuring unit the composition of the examined body tissue can be determined. Based on these results the capillary oxygen saturation of the tissue can be determined from the oximetric signals by means of the evaluation unit of the measuring device.

An expedient advancement of the inventive measuring device provides for the bioelectric impedance measuring unit to be designed such that it additionally detects global tissue parameters, such as the global fat content and/or global water content. This further enhances the functionality of the measuring device according to the invention. The bioelectric impedance measuring unit of the inventive measuring device can be designed in such a manner that it is capable of ascertaining both local as well as global tissue parameters.

The composition of the body tissue may also be determined by means of the inventive measuring device by optical methods. For this purpose, the unit for the detection of local tissue parameters may embrace an optical radiation source and a photosensor. The principle of determining the body fat content optically by means of infrared light is known from prior art.

In accordance with an advantageous configuration the inventive device comprises a heat sensor for the determination of heat dissipating via the skin surface, with the evaluation unit being designed to determine the local metabolic parameters taking signals received from the heat sensor into account. Preferably, the heat sensor enables a spatially, time and depth resolved heat measurement to be performed at the measuring site. The heat exchange or transfer data so obtained thus provides information about the local metabolic activity. Moreover, the heat sensor is suited to determine the local blood perfusion. With respect to furnish more detailed background information in this context reference is made to a publication by Nitzan et al. (Meir Nitzan, Boris Khanokh, "Infrared Radiometry of Thermally Insulated Skin for the Assessment of Skin Blood Flow", Optical Engineering 33, 1994, No. 9, pages. 2953 to 2956). Altogether, the heat sensor furnishes data that can advantageously be used for the determination of metabolic parameters for the purposes of the invention.

Depending on the type of tissue examined the arterial oxygen saturation ($SaO_2$) and the venous oxygen saturation ($SvO_2$) govern the capillary (arteriovenous) oxygen saturation ($StO_2$). The following applies:

$$K^*SvO_2+(1-K)^*SaO_2=StO_2,$$

where K is a tissue-related correction factor that depends on the volume relationship between arteries and veins in the examined tissue. This value is slightly below 0.5 on average. According to the invention, the value that has relevance to a given tissue can be determined by bioelectric impedance measurement so that the venous oxygen saturation can then be established via the formula indicated above. By measuring the heat and/or bioelectric impedance (impedance plethysmography) it is possible to determine the perfusion V, i.e. the perfusion-related volume fluctuation of the tissue. According to the relation $$VO_2=V^*(SaO_2-SvO_2)$$

the local oxygen consumption $VO_2$ can then be determined which is a measure of the metabolic activity at the measuring site.

Moreover, the measuring device according to the invention may also incorporate an optical sensor for the spatially resolved determination of the skin complexion. Diseases such as inflammations, melanoma etc. may also be detected through local discoloration of the skin.

By providing an additional ECG unit for the detection of relevant ECG signals via two or more electrodes the functionality of the inventive measuring device is advantageously enhanced. As provided for by the invention the measuring device is designed to jointly detect and evaluate plethysmographic signals and ECG signals. The evaluation unit of the measuring device in this case may advantageously be designed to evaluate the time characteristics of the volume pulse signals and the ECG signals. By means of a suitable program control feature the evaluation unit of the inventive measuring device is thus capable of automatically detecting the R peaks in the ECG signal. In this way the exact time characteristics of the heartbeat can be determined automatically. Furthermore, as a result of its program control feature the evaluation unit is also capable of recognizing the maxima in the volume pulse signal. Based on the maxima in the volume pulse signal the arrival time of the pulse wave initiated during a cardiac cycle can be detected at the peripheral measuring site examined with the measuring device. In this way, the time interval between an R peak in the ECG signal and the maximum that follows in the volume pulse signal can thus be determined. This time interval is to be regarded as an indicator for the so-called pulse wave velocity. Based on pulse wave velocity it is possible to obtain information about the blood pressure. More specific: if the pulse wave velocity is found to be higher this is indicative of a blood pressure increase while from a lower pulse wave velocity it can be concluded that there is decrease in blood pressure. However, an exact determination of the blood pressure based on pulse wave velocity is not possible, only tendencies can be indicated. Moreover, pulse wave velocity also depends on the blood density and in particular the elasticity of the blood vessel walls (for example the aorta). From the elasticity of the blood vessels in turn conclusions can be drawn as to whether arteriosclerosis may be involved. Such an evaluation or assessment may also include absolute heart rate values, heart rate variability and the respective arrhythmias of the heart. In this way, arrhythmia such as sinus tachycardia, sinus bradycardia, sinus arrest and so-called escape beats can also be detected automatically. By way of the ECG signal information can also be obtained as to the contraction time of the heart's atria during a cardiac cycle, the duration of a ventricular contraction as well as the duration of ventricular relaxation etc. Moreover, preliminary diagnoses can be made with a view to detecting blocks disturbing the conductance of the electrical excitation signals at the heart (AV block, bundle branch block etc.) and also circulatory disorder or infarction. Further irregularities in the pulse characteristics can be identified on the basis of the volume pulse signal.

Due to the combined evaluation of the ECG signal and the volume pulse signal in automatic assessment mode the inventive measuring device is capable of automatically performing a functional assessment of a patient's vascular system. On the basis of the automatically evaluated signals the inventive device is capable of roughly estimating the (global) cardiovascular condition or the fitness of a user in general and in the event of indications suggesting arteriosclerosis or other cardiovascular problems a warning signal to this effect or an easily comprehensible fitness or risk indicator can be generated for the user of the device. Therefore, the measuring device according to the invention can be advantageously employed for self-diagnostic purposes to detect cardiovascular diseases.

Of particular advantage is the inventive combination of the above described measuring methods, that is oximetry, bioelectric impedance measurement and heat measurement. By means of the evaluation unit of the device all measuring signals can be assessed to determine the arterial, capillary and venous oxygen saturation and on the basis of this data gather information about the local metabolic activity. In this way, a high efficiency and reliability of detection and localization of pathological changes is achieved. This can even be enhanced by taking into account local skin complexion parameters. As mentioned hereinbefore the additional ECG measurement permits conclusions as to the status of the user's cardiovascular system. It is also viewed beneficial to combine all parameters into a global index that is easily comprehensible for the user and provides direct and substantiated information about his or her general health condition.

Moreover, the inventive device may be provided with a data transmission interface to transfer the parameters determined by means of the evaluation unit to a personal computer (of the physician), for example via the internet, or to another device. This interface may be a customary wired or a wireless interface (working, for example, according to the DECT, GSM, UMTS or bluetooth standard). A data transmission via infrared data communication or ultrasonic methods is also conceivable.

A particularly expedient configuration of the inventive measuring device is achieved by providing said device with a storage unit for storing the parameters determined by means of the evaluation unit. By making use of the storage unit not only the course of a disease but also the effects of an administered therapy may be monitored and documented. Moreover, the data saved in said storage unit may be retrieved and assessed by the attending physician who will thus be able to carry out a detailed diagnostic investigation of the condition of the patient. It is, furthermore, expedient if the inventive device is provided with a diagnostic unit for the assessment of the parameters determined by means of the evaluation unit and recording of parameter changes, with site and time of the measurements being taken into account. Accordingly, the inventive device is of modular design. The evaluation unit is exclusively meant to assess the detected signals and based on these signals determine the parameters required for diagnostic purposes in the manner described hereinbefore. These parameters are then to be processed by the diagnostic unit to enable conclusions to be drawn as to diseases that may exist. Especially if the measuring device is employed by a user for self-diagnosis it is furthermore the purpose of the diagnostic unit to automatically detect a disease and, if necessary, alert the user by generating an appropriate warning signal.

Expediently, the diagnostic unit of the measuring device according to the invention is thus designed to determine the status of the cardiovascular system based on parameters ascertained by means of the evaluation unit. As per an especially advantageous configuration of the invention the diagnostic unit is moreover designed to calculate a global fitness index on the basis of the cardiovascular system status and the global tissue parameters (determined via bioelectric impedance measurement). The global tissue parameters may thus be utilized to obtain the global fitness index which provides especially informative advice about the current health status of the user. For the determination of the global fitness index all measured values determined for a given user may be utilized. If thought necessary, average data may be established for a selectable period of time. Aside from cardiovascular measuring values and global tissue parameters (global fat content, global water content) also the local tissue parameters as well as the local metabolic parameters (e.g. local oxygen consumption) can be taken into account. The result thus obtained expresses the global fitness index in the form of a single value that can be very easily interpreted by the user of the measuring device.

At least the optical measuring unit of the inventive measuring device operates on the basis of optical measuring processes. For this reason the device should at least be provided with one radiation source for the body tissue to be examined by exposure to electromagnetic radiation and at least one radiation sensor for the determination of the electromagnetic radiation scattered and/or transmitted by the tissue of the body. As radiation sources customary light emitting diodes or laser diodes capable of emitting optical radiation, i.e. light in the respective spectral range may be employed. It has turned out to be especially beneficial if by means of the inventive device the radiation absorption in the examined body tissue is measured at least three different light wavelengths with a view to determining the oxygen concentration of the blood and the perfusion of the tissue.

As per an expedient configuration the optical measuring unit of the inventive measuring device is provided with at least two radiation sensors for the detection of the radiation scattered and/or transmitted by the body tissue, with said radiation sensors being arranged at different distances to the radiation source. This enables conclusions to be drawn with respect to the distance the radiation has traveled in the body tissue in each case. On this basis, the oxygen concentration in the blood and in the tissue can be examined in tissue layers at different levels. Conducive to this task is the fact that the measuring signals from deeper tissue layer levels are more strongly influenced by arterial blood whereas in the near-surface regions the blood in capillary vessel system has a more pronounced influence on radiation absorption.

Advantages are offered by a configuration of the inventive measuring device which is provided with at least two radiation sources by means of which different volume ranges of the examined body tissue are exposed to radiation. This enables a differential measurement of the light absorption in a simple manner. Furthermore, metabolism-induced changes of the perfusion of the examined body tissue with oxygen-rich or oxygen-deficient blood can be investigated in this way. Helpful in this context is that the local oxygen consumption varies as a function of the metabolic activities of the tissue. The determination of the variable oxygen consumption in turn permits conclusions about the local energy consumption which directly correlates with the oxygen consumption. Of special interest is that this again allows conclusions to be drawn as to the glucose level. In this manner, the inventive measuring device also offers advantages in that the blood glucose level can be determined in a non-invasive way.

The two radiation sources of the inventive measuring device's optical measuring unit should designed such that the relevant volume areas irradiated by them are differently covered with respect to the perfusion with oxygen-deficient and oxygen-rich blood. This may be achieved, for example, by arranging for the at least two radiation sources to have different spatial radiation characteristics. Accordingly, a light-emitting diode and a laser may be employed, for example, as radiation sources which have similar wavelengths (e.g. 630 nm and 650 nm). However, the two radiation sources differ with respect to their total beam angles. Whereas the light-emitting diode irradiates the examined body tissue at a large total beam angle the light of the laser diode enters the body tissue at a very small beam angle. This results in the two radiation sources covering different volume areas of the body tissue. On account of the light-emitting diode's large total beam angle a larger volume area of the non-perfused epidermis is covered than is the case with the laser. The non-perfused epidermis remains practically unaffected by a change of the hemoglobin concentration. Accordingly, the intensity of the light-emitting diode's radiation scattered and/or transmitted by the body tissue depends less pronouncedly on a change of the hemoglobin concentration than is the case with the intensity of the radiation emitted by the laser. Prerequisite to this is that the wavelength of the radiation emitted by the two sources is selected such that the radiation is absorbed to a varying degree by oxihemoglobin and deoxihemoglobin. The wavelength should therefore range between 600 and 700 nm, preferably between 630 and 650 nm.

The evaluation unit of the inventive measuring device may beneficially be designed to enable at least one local metabolic parameter to be determined from the radiation emitted by the two sources scattered and/or transmitted by the body tissue. If oxygen is consumed in the examined body tissue oxihemoglobin is converted into deoxihemoglobin. By comparing the radiation emitted by the two sources originating from different volume areas of the body tissue a change in the concentration relation between oxihemoglobin and deoxihemoglobin can be ascertained. In this manner data about the local oxygen consumption is obtained and from this the blood glucose level can be determined. In this way, the evaluation unit of the inventive measuring device is thus expediently designed for the determination of the local oxygen consumption and/or blood glucose level based on the intensities of the radiation emitted by the two sources scattered and/or transmitted by the body tissue.

In line with an especially advantageous configuration all components of the measuring device according to the invention are accommodated within a common casing. On one end of the casing the device is provided with a measuring head fitted with the required measuring sensors. In this manner the measuring device may be carried by hand and utilized either by the user himself or by the attending physician in order to systematically examine the whole body to detect pathological changes. An indicator unit should be integrated into the casing by means of which the local oxygen consumption of the blood and/or local metabolic parameters ascertained in accordance with the invention can be made visible to the physician or user.

The measuring head of the inventive measuring device expediently embraces at least one optical radiation source and at least two sensors which are arranged on the measuring head at different distances to the radiation source. Light with different light wavelengths is generated by means of the radiation source. The radiation scattered back from the examined body tissue is measured by means of the sensors so that based on radiation absorption data conclusions can be drawn as to the oxygen concentration. The sensors arranged at different distances to the radiation source enable the radiation absorption to be examined at different tissue layer levels as explained above. In this way it is possible to distinguish the oxygen concentration in the tissue from the arterial oxygen concentration.

The measuring head of the measuring device according to the invention may also accommodate electrodes for the bioelectric impedance measurement and for ECG measurement. For a two-point measurement another ECG electrode can be integrated into the casing of the measuring device. This additional ECG electrode may also be utilized for bioelectrical impedance measurement, that is for the measurement of global tissue parameters such as global fat content and/or global water content. The electrodes shall expediently be arranged in such a way that a bioelectric impedance measurement can be carried out from one arm of the user to the other arm. Furthermore, integrated into the measuring head can be at least one heat sensor for the determination of heat dissipated through the skin surface. Considered particularly convenient for the inventive measuring device is to combine into a single measuring head the measuring sensors required for the different measuring processes (oximetry, bioelectric impedance measurement, heat measurement, ECG, measuring the skin complexion). This configuration of the measuring head enables all of the measuring values to be simultaneously detected at the relevant locations where measurements are desired.

The inventive measuring device may be of miniature design and integrated in an object worn on the user's body, with said objects being, for example, a watch, a glasses frame or a piece of clothing. In this way it will be possible to continuously monitor the health status.

The invention, furthermore, relates to a method of collecting and evaluating physiological parameters, said method providing for oximetric and/or plethysmographic measuring signals from body tissue to be collected by means of an optical measuring unit, and the oximetric and plethysmographic measuring signals to be processed by means of an evaluation unit for the purpose of determining the pulse and/or the local oxygen concentration.

With the aid of such a method the objective of the invention is thus reached by providing for the evaluation unit to ascertain on the basis of oximetric signals at least one local metabolic parameter, in particular the local oxygen consumption.

Expediently, additional local tissue parameters such as fat content, water content and/or perfusion are collected/detected with the at least one local metabolic parameter being determined on the basis of the oximetric signals and the local tissue parameters. The local tissue parameters can be collected by means of bioelectric impedance measurement, optically or by means of heat measurement. It is also considered expedient to additionally collect/detect an ECG signal. By means of the evaluation unit a cardiovascular parameter can be determined from the plethysmographic measuring signals and the ECG signal. It is especially expedient as stated hereinbefore to collect additional global tissue parameters such as fat content and/or water content. This enables a global fitness index to be calculated based on the cardiovascular parameters obtained via the evaluation unit and the global tissue parameters. A particularly advantageous variant of the inventive method provides for different volume areas of the examined body tissue to be irradiated by means of the optical measuring unit, with—as described above—the at least one local metabolic parameter being determined on the basis of the radiation scattered and/or transmitted by the body tissue in the different volume areas. For this purpose the optical measuring unit may embrace at least two radiation sources with different spatial radiation characteristics, with the local oxygen consumption and/or the blood glucose level being determined based on the intensity of the radiation of the two radiation sources scattered and/or transmitted by the body tissue.

An exemplary embodiment of the invention is illustrated by way of the following drawings where FIG. 1 is a schematic view of the inventive measuring device with the measuring head shown as an enlarged representation;

Figure 1:
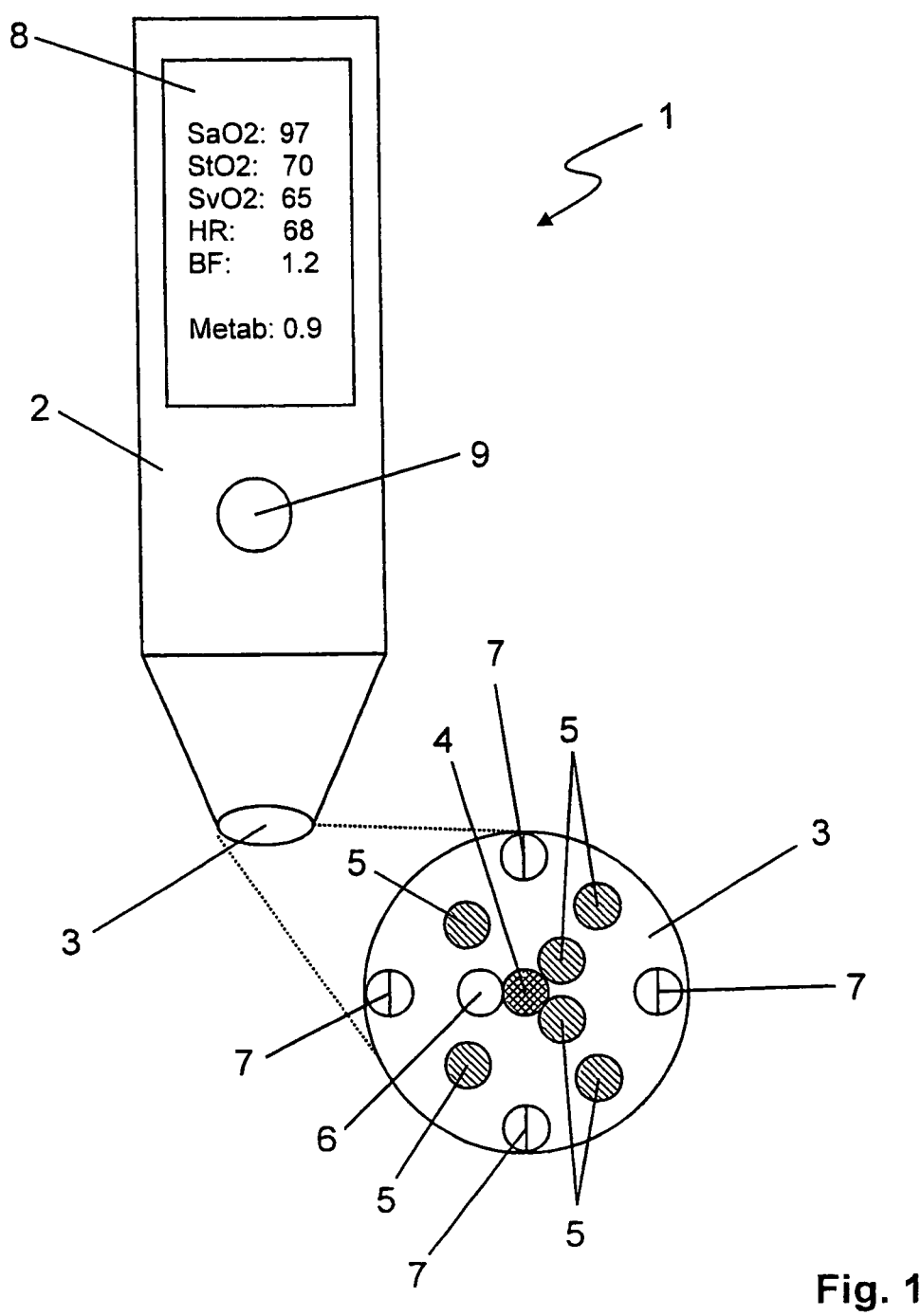

In FIG. 1 the inventive measuring devices altogether is identified by reference number 1. All components of the device are accommodated in a common casing 2 so that the unit may be put to use manually at various optional measuring sites on the body of a user. At the front end of casing 2 a measuring head 3 is arranged into which the various measuring sensors of the device 1 are integrated. When the measuring device 1 is used these are placed on the skin surface of the user at the measuring location. The measuring head is provided with a centrally arranged light-emitting diode 4 capable of emitting light at different wavelengths. For this purpose, various light-emitting semiconductor elements for example may be accommodated in a common enclosure of the light-emitting diode 4. It is also conceivable to use optical fiber arrangements to bring the light from the various light sources to the bottom of the measuring head 3. Moreover, the measuring head 3 is provided with a total of six photosensors 5 arranged at various distances to the light source 4. Two of the photosensors 5 are arranged immediately adjacent to light source 4. Two other sensors 5 are located at a medium distance to the light source 4 whereas the two remaining sensors 5 are arranged at a maximum distance to light source 4. Sensors 5 arranged immediately adjacent to the light source 4 primarily receive light scattered from or at the upper skin layers of the user. On the other hand, the sensors 5 located farther away from light source 4 are suited to measure the light absorption in deeper tissue layers. Furthermore, a heat sensor 6 is located close to the light source 4. This arrangement ensures that the determination of the blood perfusion based on heat measurement takes place at the same measuring location as the optical measurement. On the outside of the measuring head 3 four electrodes 7 are arranged which are used to measure the local bioelectrical impedance. The electrodes are each divided in two and consist of two separate contact faces electrically isolated from each. One of the two contact faces in each case serves to apply an electric current at the measuring site whereas the other contact face is used for voltage measurement. In this way it is ensured that the measuring results are not impaired by the contact resistances of the measuring electrodes. When carrying out the bioelectric impedance measurement the four electrodes 7 may be used in various combinations conducive to optimizing the reliability of the measuring results. At least one of the electrodes 7 is also used as ECG electrode of an ECG unit of the measuring device 1. An LCD display 8 serving as indicating unit is integrated into the casing 2 of the measuring device 1. The LCD display 8 serves to indicate the local oxygen concentration of the blood. In this case the arterial ($SaO_2$), the capillary ($StO_2$) and the venous ($SvO_2$) oxygen concentrations are indicated. The determined heart rate (HR), the locally determined fat content of the tissue (BF) are also indicated. A local metabolic parameter is furthermore indicated that reflects the metabolic activity at the measuring location. Moreover, an on/off switch 9 is provided on casing 2 which serves to activate or deactivate the device in the usual manner. The actuating surface of the on/off switch 9 furthermore constitutes the contact face of another ECG electrode which enables a simple two-point derivation of the ECG signal of the user of the device. Aside from this the contact surface enables an arm-to-arm measurement of global tissue parameters such as global fat content and/or global water content by means of bioelectric impedance measurement.

Figure 2:
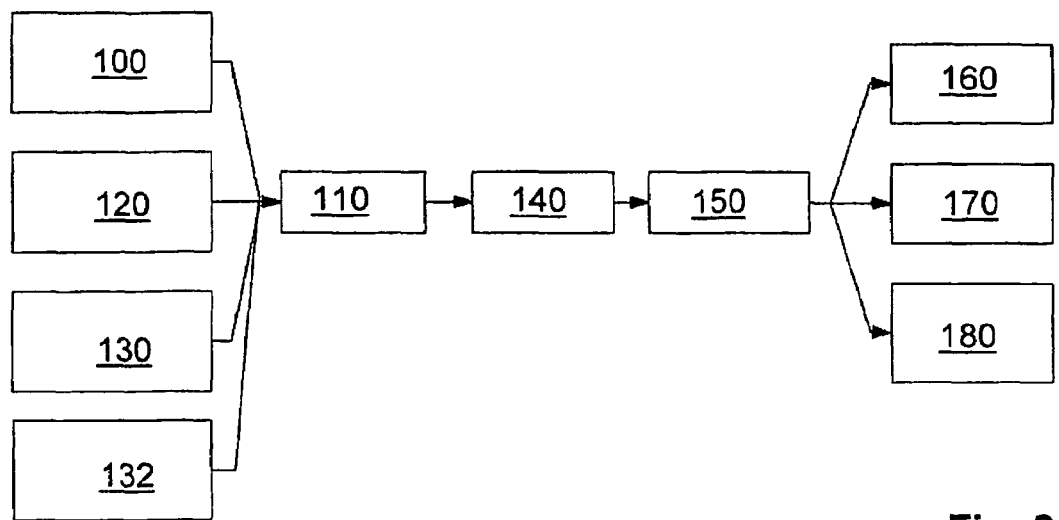
FIG. 2 is a representation of the inventive device in the form of a block diagram.

FIG. 2 is a schematic representation of the configuration of the inventive measuring device in the form of a block diagram. Device 1 embraces an optical measuring unit 100 for the optical measurement of the oxygen concentration in the blood vessel system of the body tissue at the respective measuring site. Moreover, the optical measuring unit 100 serves to measure the local skin complexion. The oximetric and plethysmographic signals detected by means of the optical measuring unit 100 are transferred to an analyzing unit 110. Another significant component of the device 1 is a heat measuring unit 120 which serves to determine the heat dissipated via the skin surface. The heat measuring unit 120 in this case operates in a spatially, time- and depth-resolved manner. The measuring signals detected by the heat measuring unit 120 are also transferred to the analyzing unit 110 for further processing. Measuring device 1 is also provided with an impedance measuring unit 130 serving to detect local tissue parameters by means of bioelectric impedance measurement. The measuring signals obtained via the impedance measuring unit 130 are also processed by means of the analyzing unit 110. Finally, the invention also provides for an ECG unit 132 serving to collect an ECG signal. To enable the ECG signals to be processed also the ECG unit 132 is connected with the analyzing unit 110. The light source 4 as well as the light sensors 5 of the measuring head 3 shown in FIG. 1 are assigned to the optical measuring unit 100. The heat measuring unit 120 is connected with the heat sensor 6. The impedance measuring unit 130 collects the measuring signals via the electrodes 7 of the measuring head 3. By means of analyzing unit 110 all measuring signals are pre-processed. For this purpose the signals go through a bandpass filter to eliminate interference in the range of the mains frequency of 50 or 60 Hz. Moreover, the signals are subjected to a noise suppression step. Having passed through the analyzing unit 110 the processed signals of the optical measuring unit 100, the heat measuring unit 120, the impedance measuring unit 130 and the ECG unit 132 are transferred to an evaluation unit 140. Purpose of evaluation unit 140 is to calculate from the measuring signals the parameters that are important for diagnosis. From the time-related measuring signals of impedance measuring unit 130 first the composition of the examined body tissue (water content, fat content etc.) is calculated. From the signals of the optical measuring unit 100 the arterial oxygen saturation and—based on the tissue parameters previously determined via the impedance measurement—the capillary oxygen saturation are calculated. Moreover, from the measuring signals of heat measuring unit 120 and from the plethysmographic data that can be derived from the time-related impedance measurement the blood perfusion and the arterial temperature are determined. From the results of all the calculations thus carried out the venous oxygen saturation and from that further metabolic parameters are calculated by means of evaluation unit 140, in particular the local oxygen consumption at the measuring location. Furthermore, the evaluation unit 140 serves to determine at least one cardiovascular parameter from the plethysmographic data and the ECG signal. The calculation results are interpreted with the aid of a diagnostic unit 150. The diagnostic unit 150 serves to assess the local metabolic and cardiovascular parameters calculated by means of evaluation unit 140, and record parameter changes with the respective site measurements being taken into account. The diagnostic unit 150 is designed such that said it automatically recognizes on the basis of the calculation results of evaluation unit 140 characteristics indicative of a possible disease such as, for example, an inflammation, cancer disease or arteriosclerosis. A user of the measuring device 1 may then be alerted to this by providing relevant information via the indicator unit 8 of the device 1. Such information may, for instance, be furnished in the form of a global index parameter via indicator unit 8 that can be easily and unambiguously interpreted and allows a conclusion as to the probability of a given disease. For the purpose of displaying the measuring results the evaluation unit 140 and the diagnostic unit 150 are connected with a graphics unit 160 which in turn acts on the indicator unit 8 of the measuring device 1. The data obtained can be stored by a storage unit 170 with both the date and the time of the respective measurement being saved simultaneously. Moreover, an interface unit 180 is provided which serves to connect the measuring device 1 with a computer or another communication system. Via the interface unit 180 all the data and parameters, in particular the data and parameters stored by the storage unit 170, may be transmitted to a PC—not shown in the figure—of the attending physician where the data may be subjected to a detailed analysis. In particular, data and parameters recorded by the device 1 over a prolonged period of time may be investigated for changes to enable conclusions to be drawn with respect to the development of an existing disease. Furthermore, there is the possibility that the inventive measuring device 1 is used as a mere measuring data collecting and transmitting unit with the recorded signals being directly transmitted to the PC of the physician. The relevant evaluations and calculations may then be performed by the PC in a faster and more comfortable way.

Figure 3:
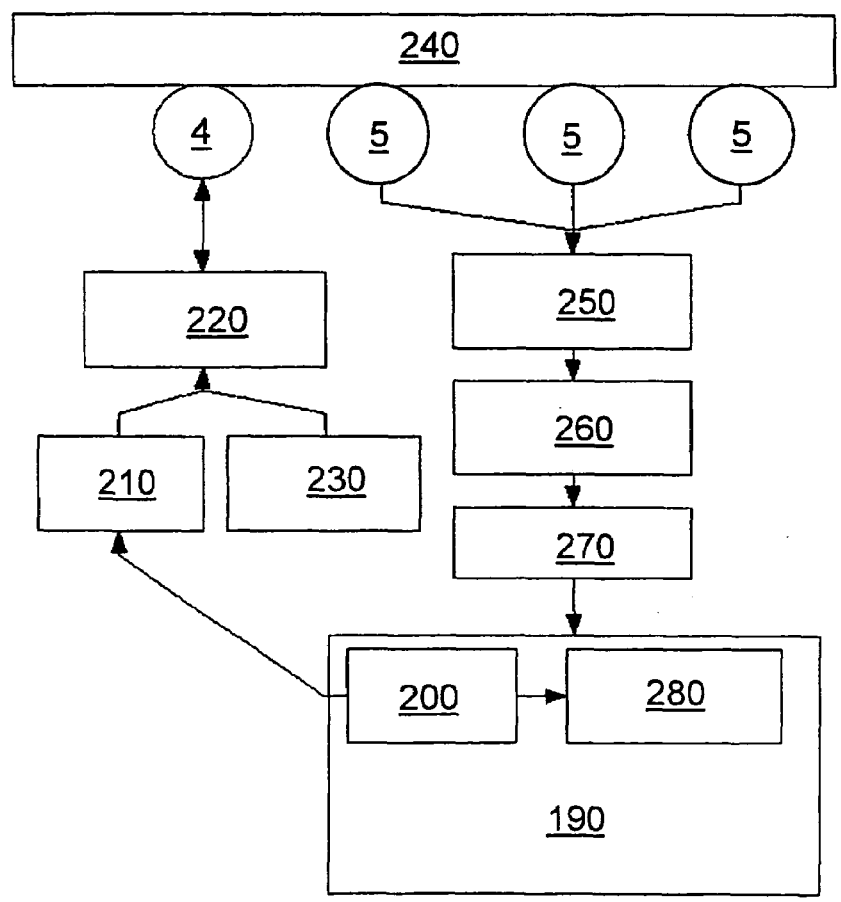
FIG. 3 is a block diagram representation of the oximetry unit of the inventive measuring device.

FIG. 3 illustrates the configuration of the optical measuring unit 100 of the inventive device 1 with said optical measuring unit 100 embracing a microcontroller 190. Part of the microcontroller 190 is a timing generator 200 which generates control signals transmitted to a modulation unit 210. This enables the time modulation of the light emission of the light-emitting diode 4 to be controlled. Light-emitting diode 4 is connected to the modulation unit 210 via a control unit 220. The intensity of the light emitted by the diode 4 can, moreover, be adjusted via a power control unit 230. Light-emitting diode 4 is also capable of sending out light of at least three different wavelengths. To make this possible various light emitting semiconductor components are combined in a single enclosure of the light-emitting diode 4. The time sequence of the light emission with the different light wavelengths is controlled by means of timing generator 200. The photosensors 5 integrated into measuring head 3 of the device 1 as well as the light-emitting diode 4 are in contact with the user's body tissue 240 as schematically illustrated in FIG. 3. In the body tissue 240 the light emitted by diode 4 is scattered and absorbed according to the oxygen concentration of the blood flowing through the tissue 240. The scattered light is detected by photosensors 5. The photoelectric current of each photosensor 5 is converted into voltage by means of converter 250, amplified by means of amplifier 260 and converted into digital measuring signals with the aid of an analog/digital converter 270. The digital signals are then fed to a demodulator 280 which is part of the microcontroller 190. Demodulator 280 serves to separate the recorded measuring signals according to the relevant light wavelengths and different distances between photosensors 5 and the light-emitting diode 4. Finally, the signals are transferred to the analyzing unit 110.

Figure 4:
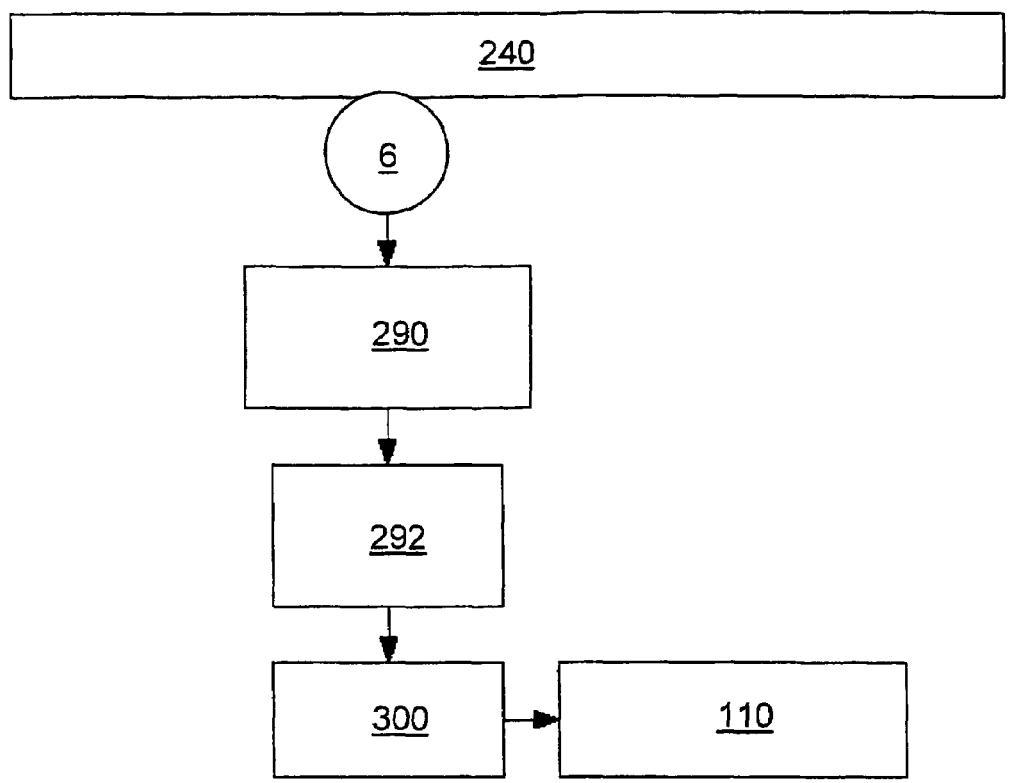
FIG. 4 is a block diagram representation of the heat measuring unit.

The configuration of the heat measuring unit 120 of the inventive measuring device is described based on the illustration in FIG. 4. The heat sensor 6 in contact with body tissue 240 is provided with several temperature measuring elements as well as a heat-conducting element which are not shown in the illustration. As soon as the sensor 6 is in contact with tissue 240 an exchange of heat commences. By means of temperature measuring elements the temperature is measured at various locations via the heat-conducting element of sensor 6. With this data the heat locally dissipated by tissue 240 can be determined (in a spatially, time- and depth-resolved manner). The signals collected via the temperature measuring elements pass through impedance converter 290 as well as amplifier 292 following which they are digitized by means of an analog/digital converter 300. For further processing the digital measuring signals are then transmitted to the analyzing unit 110. A suitable heat sensor 6 has been described, for example, in the publication prepared by Ok Kyung Cho et al. (Ok Kyung Cho, Yoon Ok Kim, Hiroshi Mitsumaki, Katsuhiko Kuwa, "Noninvasive Measurement of Glucose by Metabolic Heat Conformation Method", Clinical Chemistry 50, 2004, No. 10, p. 1894 to 1898).

Figure 5:
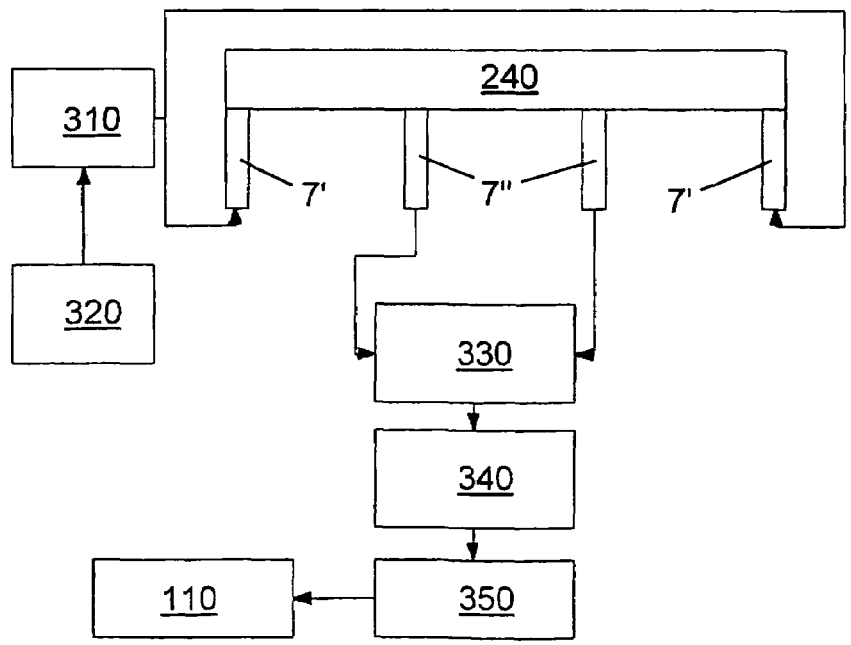
FIG. 5 is a block diagram representation of the impedance measuring unit of the measuring device.

FIG. 5 shows the configuration of the impedance measuring unit 130 of the measuring device 1 according to the invention. The impedance measuring unit 130 comprises several electrodes 7. Via contact faces 7' an alternating current is applied to the body tissue 240 to be examined, said current being generated by means of a power source 310. Power source 310 is controlled by a sine-wave generator 320. The frequency of the alternating current varies between 20 kHz and 100 kHz. Via contact faces 7" a voltage measuring signal is picked off at the body tissue 240. From the relation between the voltage measured and the current applied conclusions can be drawn as to the local impedance of the body tissue 240. For this purpose the voltage is increased by an amplifier 330 and filtered by means of a filter 340 to eliminate interference signals. Again a digitization is now performed by means of an analog/digital converter 350. The digitized measured values are then transmitted to the analyzing unit 110 where they are processed.

Figure 6:
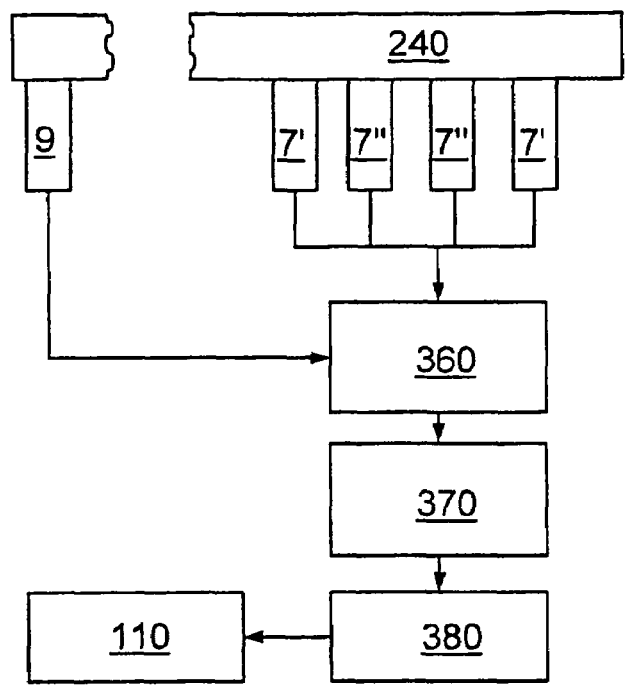
FIG. 6 is a block diagram representation of the ECG unit of the measuring device.

The configuration of the ECG unit 132 of the inventive measuring device is elucidated based on the illustration in FIG. 6. The ECG unit 132 collects ECG signals via ECG electrodes 7' and 7". These are the electrodes of the impedance measuring unit 130. In the exemplary embodiment illustrated electrodes 7' and 7" thus have a double function. For a useful two-point derivation of the ECG signal another ECG electrode 9 is required which comes into contact with the body of the user at a location sufficiently away from electrodes 7' and 7". In the embodiment example shown, the ECG electrode 9 simultaneously serves as control surface of the on/off switch of the measuring device 1. All electrodes are thus integrated into the measuring device 1. Separate electrodes, e.g. those connected via cables, are not considered mandatory (for a simple two-point derivation of the ECG signal). In lieu of the control surface of the switch of the measuring device 1 an additional electrode may as well be arranged on the casing 2 of the measuring device 1. The derived ECG signal is processed by means of amplifier 360 and filter 370. Having passed through another analog/digital converter 380 the signal is transmitted to the analyzing unit 110.

Figure 7:
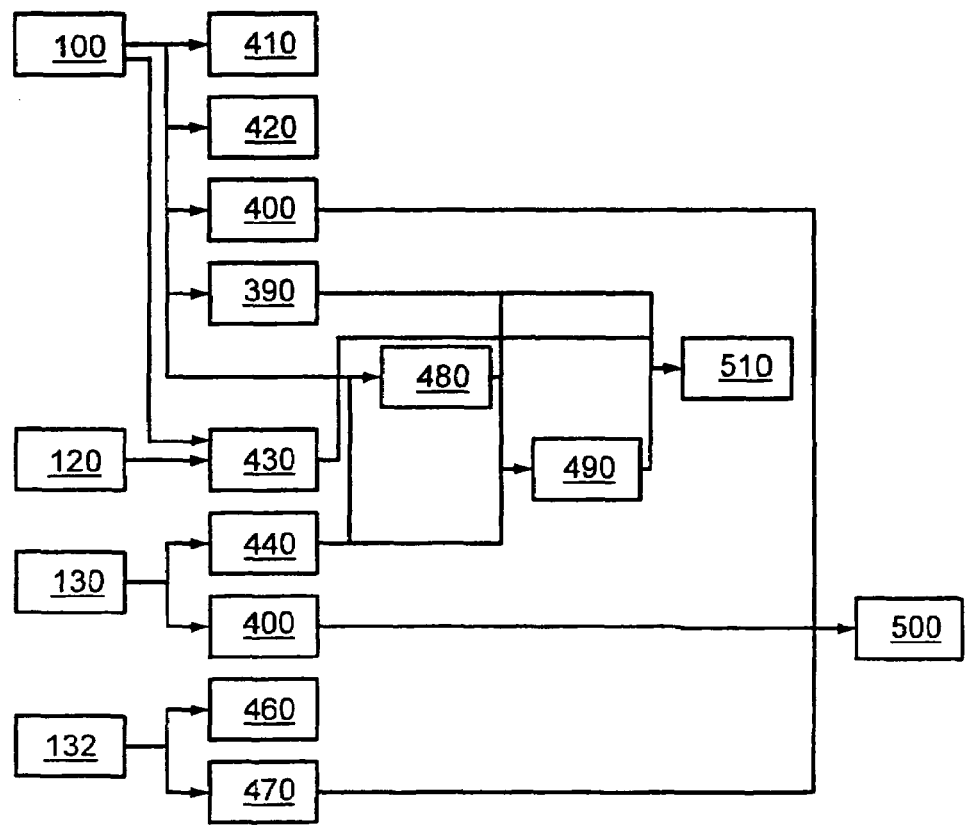
FIG. 7 represents the signal evaluation by means of the inventive measuring device.

How to determine the physiological parameters in accordance with the invention can be seen from FIG. 7. The optical measuring unit 100 delivers by pulse oximetry an arterial oxygen saturation value 390, by photoplethysmography a volume pulse signal 400, and by reflection/absorption measurement a skin complexion value 410. Moreover, the optical measuring unit 100 supplies a differential value 420 between the systolic and diastolic volume pulse. The perfusion 430 is determined by means of heat measuring unit 120. Simultaneously, perfusion 430 data may also be obtained via the optical measuring unit 100. The signals of the impedance measuring unit 130 yield the local tissue parameters 440 and also the volume pulse 400. The ECG unit 132 furnishes data 460 about arrhythmias that might exist and about the conductance at the cardiac muscle. Moreover, the actual ECG signal 470 with cardiac activity time characteristics is available. On the basis of the tissue parameters 440 and the arterial oxygen saturation 390 the capillary, i.e. the arteriovenous oxygen saturation 480 is determined. By also taking tissue parameters 440 into account the venous oxygen saturation 490 is then determined on this basis. From the cardiac cycle time characteristics 470 and the time characteristics of the volume pulse signals 400 the pulse wave velocity 500 can be determined. From these data information can be furnished with respect to the general cardiovascular condition (the fitness) of the user. In this case, a cardiovascular index is determined based on the arrhythmias 460, the pulse wave velocity 500 and the difference between systolic and diastolic volume pulse 420. In calculating the index the local oxygen consumption 510 is furthermore taken into account which is obtained from data of the perfusion 430, the arterial oxygen saturation 390 and the venous oxygen saturation 490. The complexion value 410 and the body fat content 440 are also taken into account.

Figure 8:
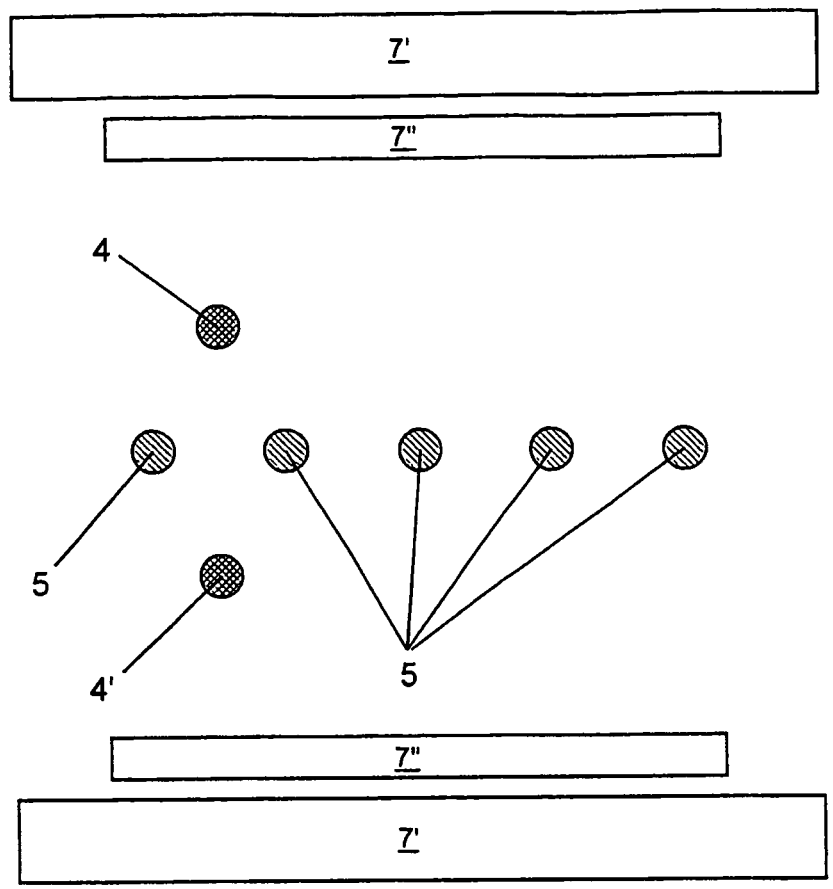
FIG. 8 is a schematic representation of an alternative arrangement of radiation sources, radiation sensors and electrodes for the bioelectric impedance measurement with the inventive measuring device.

In FIG. 8 an alternative sensor arrangement of the inventive measuring device is illustrated. Similar to the representation in FIG. 1 FIG. 8 shows a view of the measuring head surface to be brought into contact with the skin of a user of the measuring device. The representation in FIG. 8 is significantly enlarged. The surface needed for the sensor elements may be as small as approximately 0.5 to 2 cm$^2$.

In the exemplary embodiment depicted in FIG. 8 two radiation sources 4 and 4' are provided which irradiate different volume areas of the body tissue to be examined. For this purpose the two radiation sources 4 and 4' have different spatial radiation characteristics, i.e. different dispersion angles or beamwidths. Radiation source 4 is a light-emitting diode whereas a laser is employed as radiation source 4', for example a so-called VCSEL laser (vertical cavity surface emitting laser). Both the light-emitting diode 4 and the laser 4' emit light of very similar wavelength (e.g. 630 nm and 650 nm) but at different beam angles (e.g. 25° and 55°). As has been described above, the arrangement shown in FIG. 8 enables a differential measurement of metabolism-induced changes of the oxygen content of the blood to be carried out. For this purpose the wavelength of the radiation emitted by each of the two radiation sources 4 and 4' must be in a range in which the light of oxihemoglobin and deoxihemoglobin is absorbed differently. For an absolute measurement of the oxygen content of the blood (oxygen saturation) further radiation sources (not included in FIG. 8) must be provided the light wavelength of which is in a spectral range where the light absorption of oxihemoglobin and deoxihemoglobin is mainly identical (so-called isobectic point). The light emitted by the light-emitting diode and laser may be conducted to the respective location on the measuring head with the help of suitable optical fibers. In such a case FIG. 8 shows the relevant fiber ends which have reference numbers 4 and 4'. It is possible to connect the light-emitting diode and the laser to the respective fibers in such a way that they irradiate the body tissue to be examined at the desired different beam or opening angles. Accordingly, different body tissue volumes are examined with the two radiation sources. On account of the larger beam angle the proportion of the non-perfused epidermis of the body tissue examined by means of the light-emitting diode is greater than with the laser. The light of radiation source 4 and radiation source 4' scattered and to some extent absorbed by the body tissue is detected with the aid of radiation sensors 5 arranged at distances equally spaced to each other. Said sensors may be photodiodes. Preferably, the photodiodes are not arranged directly on the surface of the measuring head. Instead, the light is conducted to the photodiodes via optical fibers. To distinguish the light of radiation source 4 from the light emitted by radiation source 4' the two light sources 4 and 4' may be operated differently in a time modulated fashion with the signals detected via the sensors 5 being demodulated as required. An alternative approach is to distinguish the radiation emitted by the two radiation sources 4 and 4' on the basis of different wavelengths. The intensity of the radiation emitted by the radiation sources 4 and 4' weakens as a function of the length of travel when passing through body tissue, with the relationship existing between intensity attenuation and the concentration of the absorbing substance (oxygenated hemoglobin) being defined by the known Lambert-Beer law. By means of the equidistantly arranged sensors 5 shown in FIG. 8 the desired parameters of the intensity attenuation can be determined with great accuracy, that is tenuation can be determined with great accuracy, that is separately for the volume areas of the examined body tissue covered by each of the radiation sources 4 and 4'. The intensity attenuation parameters assigned to the different radiation sources 4 and 4' can be related to each other by means of the evaluation unit of the inventive measuring device to enable a differential measurement to be achieved in this way. In the simplest case quotients or ratios are calculated from the intensity attenuation parameters of the radiation emitted by the two radiation sources 4 and 4'. Variations of these quotients enable conclusions with respect to changes that have occurred in the metabolism. For example, if the blood glucose level rises after food substances have been ingested the amount of glucose admitted to the cells of the body tissue increases (after a certain delay) and the glucose is converted in the cells which results in oxygen being consumed. The required oxygen is transported to the cells via the blood. In this process oxygenated hemoglobin becomes deoxygenated hemoglobin due to oxygen being released. Accordingly, the ratio of deoxygenated hemoglobin to oxygenated hemoglobin increases. Due to the differently sized beam angles of the radiation emitted by radiation sources 4 and 4' the changes in hemoglobin concentration have a different effect on the respective intensity attenuation. From the quotients of the intensity attenuation parameters changes of the hemoglobin concentration can thus be detected. It is thus possible to indirectly make conclusions as to the consumption of oxygen. Since the blood glucose level also has an influence on the oxygen consumption the differential measurement of the radiation absorption as described thus enables the blood glucose level to be determined as well. Expediently, a bioimpedance analysis is additionally performed together with the optical measurement, with the electrodes 7' and 7" illustrated in FIG. 8 being provided for this purpose. Purpose of the bioimpedance measurement is primarily to determine the local perfusion. This measurement yields further parameters on which the determination of the oxygen consumption and thus the blood glucose level may be based. In the embodiment example shown in FIG. 8 the electrodes 7' and 7" are arranged on opposite sides of radiation sources 4 and 4' and radiation sensors 5 to make sure the same area of the examined body tissue is covered by the bioimpedance measurement and optical measurement.

Figure 9:
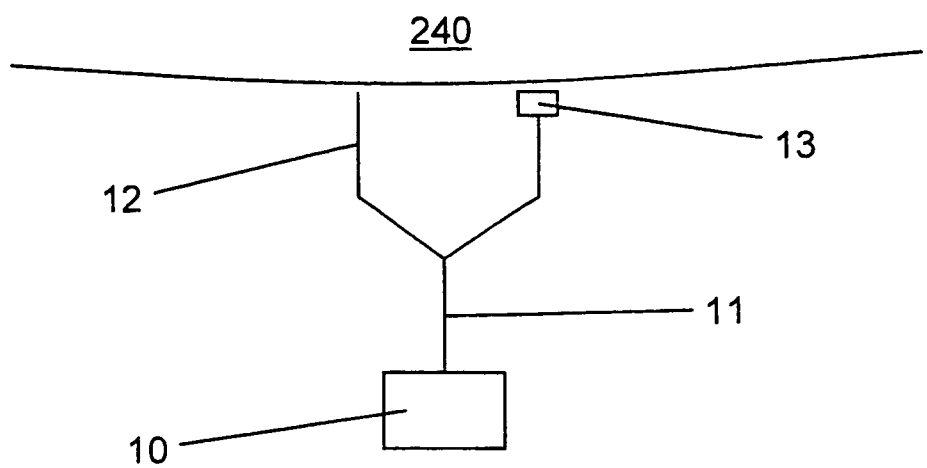
FIG. 9 shows the illustration of how an inventive measuring device with two radiation sources may be realized.

FIG. 9 illustrates a simple and cost-effective way to provide and implement two radiation sources 4 and 4' having different spatial radiation characteristics. For this purpose, a single radiation-emitting element 10, for example a light-emitting diode, is used the light of which is conducted through an optical fiber 11. At a suitable location the optical fiber is split into two fiber branches. Via fiber branch 12 the light is directly admitted to the body tissue 240 under examination. In the other fiber branch an additional optical element 13, for example a lens, is provided so that a smaller radiation angle may be obtained, for instance. Each of the fiber branches illustrated in FIG. 9 thus constitutes a radiation source 4 or 4', as represented in FIG. 8.

The invention claimed is:

1. A measuring device for non-invasive determination of physiological parameters comprising at least one optical measuring unit generating at least one of oximetric measuring signals and plethysmographic measuring signals, and an evaluation unit for processing the measuring signals, wherein the evaluation unit is designed such that at least one local metabolism parameter is determined from the signals furnished by the at least one optical measuring unit,
wherein the optical measuring unit has at least two radiation sources for irradiating the body tissue to be examined, and at least one radiation sensor for the detection of at least one of the radiation scattered by the body tissue and the radiation transmitted by the body tissue,
wherein the at least two radiation sources have different spatial radiation characteristics comprising different beam angles, and
wherein the at least two radiation sources irradiate different volume areas of the body tissue to be examined.

2. The measuring device according to claim 1, comprising a unit for the acquisition of local tissue parameters, with the evaluation unit being designed such that the at least one local metabolic parameter is determined from the signals furnished by the optical measuring unit and obtained from tissue parameters.

3. The measuring device according to claim 2, wherein the unit for the acquisition of local tissue parameters comprises a bioelectric impedance measuring unit.

4. The measuring device according to claim 3, wherein the bioelectric impedance measuring unit is designed such that it additionally detects overall tissue parameters of the body.

5. The measuring device according to claim 2, wherein the unit for the detection of local tissue parameters comprises an optical radiation source and a radiation sensor.

6. The measuring device according to claim 2, comprising a heat sensor for the determination of the heat dissipated via the skin surface, with the evaluation unit being designed to determine the local metabolic parameters taking the signals of the heat sensor into account.

7. The measuring device according to claim 2, comprising an optical sensor for the spatially resolved determination of the skin complexion.

8. The measuring device according to claim 2, comprising an ECG unit for the collection of an ECG signal via two or more ECG electrodes, with the evaluation unit being designed for the assessment of the time characteristics of the ECG signal.

9. The measuring device according to claim 8, wherein the evaluation unit is designed for at least one of the assessment of the time characteristics of a plethysmographic signal detected by the device and the determination of the pulse wave velocity based on the time characteristics of the ECG signal and the plethysmographic signal.

10. The measuring device according to claim 2, comprising a storage unit for the storage of the parameters determined by means of the evaluation unit.

11. The measuring device according to claim 2, comprising a diagnostic unit for the assessment of the parameters determined by means of the evaluation unit and recording of parameter changes, with site and time of the measurements being taken into account.

12. The measuring device according to claim 11, wherein the diagnostic unit is designed for the determination of the status of the cardiovascular system based on parameters ascertained by the evaluation unit.

13. The measuring device according to claim 11, wherein the diagnostic unit is designed for the calculation of an overall fitness index of the body on the basis of the status of the cardiovascular system and the overall tissue parameters of the body.

14. The measuring device according to claim 1, wherein the optical measuring unit is provided with at least two radiation sensors for the detection of at least one of the radiation scattered by the body tissue and the radiation transmitted by the body tissue, with the radiation sensors being located at different distances to the radiation source.

15. The measuring device according to claim 1, wherein the evaluation unit is designed for the determination of the at least one local metabolic parameter based on at least one of the radiation of the two radiation sources scattered by the body tissue and the radiation of the two radiation sources transmitted by the body tissue.

16. The measuring device according to claim 15, wherein the evaluation unit is furthermore designed for the determination of at least one of the local oxygen consumption and the blood glucose level based on the intensities of at least one of the radiation emitted by the two radiation sources and scattered by the body tissue and the radiation emitted by the two radiation sources and transmitted by the body tissue.

17. The measuring device according to claim 1, wherein the wavelength of the radiation emitted by each of the two radiation sources is in the range of between 600 and 700 nm.

18. The measuring device according to claim 1, wherein the radiation sources and the radiation sensors are arranged on a measuring head.

19. The measuring device according to claim 18, wherein the measuring head comprises electrodes for the bioelectric impedance measurement.

20. The measuring device according to claim 19, wherein at least one of the electrodes is also designed as an ECG electrode.

21. The measuring device according to claim 18, wherein the measuring head comprises at least one heat sensor.

22. The measuring device according to claim 18, wherein the measuring head is arranged at the front end of a common casing which accommodates the optical measuring unit and the evaluation unit so that the design of the entire device enables the entire device to be hand-guided.

23. The measuring device according to claim 20, wherein the casing is provided with an additional ECG electrode located on the outer side.

24. The measuring device according to claim 23, wherein the additional ECG electrode is also designed for bioelectrical impedance measurement purposes.

25. The measuring device according to claim 1, comprising an indicator unit displaying at least one of the local oxygen concentration of the blood and the at least one local metabolic parameter.

26. The measuring device according to claim 1, comprising an interface connecting the measuring device with a computer or another device.

27. The measuring device according to claim 1, wherein said device is of miniature design and integrated into an object worn on a user's body.

28. A method for the collection and evaluation of physiological parameters, the method comprising:
providing a measuring device comprising at least one optical measuring unit generating at least one of oximetric measuring signals and plethysmographic measuring signals, and an evaluation unit for processing the measuring signals, wherein the evaluation unit is designed such that at least one local metabolism parameter is determined from the signals furnished by the at least one optical measuring unit,
wherein the optical measuring unit has at least two radiation sources for irradiating the body tissue to be examined, and at least one radiation sensor for the detection of at least one of the radiation scattered by the body tissue and the radiation transmitted by the body tissue,
wherein the at least two radiation sources have different spatial radiation characteristics comprising different beam angles, and
wherein the at least two radiation sources irradiate different volume areas of the body tissue to be examined,
collecting the at least one of measuring signals selected from the group consisting of oximetric measuring signals and plethysmographic measuring signals from body tissue via the optical measuring unit
and processing the at least one of measuring signals via the evaluation unit for the purpose of determining at least one of the pulse and the local oxygen concentration,
wherein
via the evaluation unit at least one local metabolic parameter is determined.

29. The method according claim 28, wherein local tissue parameters are detected, with the at least one local metabolic parameter being determined on the basis of the oximetric signals and the local tissue parameters.

30. The method according to claim 29, wherein the local tissue parameters are detected via bioelectrical impedance measurement.

31. The method according to claim 29, wherein the local tissue parameters are detected optically.

32. The method according to claim 29, wherein the local tissue parameters are detected via spatially resolved heat measurement.

33. The method according to claim 28, comprising a detection of an ECG signal conducted in addition to the detection of the oximetric measuring signals.

34. The method according to claim 33, wherein via the evaluation unit cardiovascular parameter is determined on the basis of the plethysmographic measuring signals and the ECG signal.

35. The method according to claim 28, comprising a detection of overall tissue parameters of the body.

36. The method according to claim 34, wherein an overall fitness index of the body is calculated on the basis of the cardiovascular parameter and the overall tissue parameters of the body.

37. The method according to claim 28, wherein the at least one local metabolic parameter is determined on the basis of at least one of the radiation scattered by the body tissue in the different volume areas and the radiation transmitted by the body tissue in the different volume areas.

38. The method according to claim 37, wherein at least one of the local oxygen consumption and the blood glucose level is determined based on at least one of the intensity of the radiation of the two radiation sources scattered by the body tissue and the intensity of the radiation of the two radiation sources transmitted by the body tissue.

39. A measuring device for non-invasive determination of physiological parameters comprising at least one optical measuring unit generating at least one of oximetric measuring signals and plethysmographic measuring signals, an evaluation unit for processing the measuring signals, wherein the evaluation unit is designed such that at least one local metabolism parameter is determined from the signals furnished by the at least one optical measuring unit, and at least one electrode for at least one of a bioelectric impedance measurement and an ECG measurement,
wherein the optical measuring unit has at least one radiation source for irradiating the body tissue to be examined, and at least one radiation sensor for the detection of at least one of the radiation scattered by the body tissue and the radiation transmitted by the body tissue, and
wherein the at least one radiation source, the at least one radiation sensor, and the at least one electrode are arranged on a measuring head and take up a surface area on the measuring head in a range of 0.5 cm$^2$ to 2 cm$^2$.

* * * * *

UNITED STATES PATENT AND TRADEMARK OFFICE
CERTIFICATE OF CORRECTION

PATENT NO.         : 8,428,673 B2
APPLICATION NO.    : 11/990317
DATED              : April 23, 2013
INVENTOR(S)        : Cho et al.

It is certified that error appears in the above-identified patent and that said Letters Patent is hereby corrected as shown below:

In the Claims:

In Column 18, line 21, Claim 34, before the word "cardiovascular" please insert: --a--.

Signed and Sealed this
Third Day of September, 2013

Teresa Stanek Rea
*Acting Director of the United States Patent and Trademark Office*

UNITED STATES PATENT AND TRADEMARK OFFICE
CERTIFICATE OF CORRECTION

PATENT NO.       : 8,428,673 B2
APPLICATION NO. : 11/990317
DATED            : April 23, 2013
INVENTOR(S)      : Cho et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1383 days.

Signed and Sealed this
Eighth Day of September, 2015

Michelle K. Lee
*Director of the United States Patent and Trademark Office*